US009114145B2

(12) United States Patent
Bernick et al.

(10) Patent No.: US 9,114,145 B2
(45) Date of Patent: *Aug. 25, 2015

(54) NATURAL COMBINATION HORMONE REPLACEMENT FORMULATIONS AND THERAPIES

(71) Applicant: TherapeuticsMD, Inc., Boca Raton, FL (US)

(72) Inventors: Brian A. Bernick, Boca Raton, FL (US); Janice Louise Cacace, Miami, FL (US); Peter H. R. Persicaner, Boca Raton, FL (US); Neda Irani, Palm Beach Garden, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,946

(22) Filed: Sep. 3, 2014

(65) Prior Publication Data

US 2014/0371184 A1  Dec. 18, 2014

Related U.S. Application Data

(60) Continuation of application No. 14/099,545, filed on Dec. 6, 2013, now Pat. No. 8,846,648, which is a division of application No. 13/684,002, filed on Nov. 21, 2012, now Pat. No. 8,633,178.

(60) Provisional application No. 61/662,265, filed on Jun. 20, 2012, provisional application No. 61/661,302, filed on Jun. 18, 2012, provisional application No. 61/563,408, filed on Nov. 23, 2011.

(51) Int. Cl.
| | |
|---|---|
| *A01N 45/00* | (2006.01) |
| *A61K 9/48* | (2006.01) |
| *A61K 31/57* | (2006.01) |
| *A61K 9/16* | (2006.01) |
| *A61K 31/565* | (2006.01) |
| *A61K 9/70* | (2006.01) |

(52) U.S. Cl.
CPC . *A61K 31/57* (2013.01); *A61K 9/16* (2013.01); *A61K 9/4858* (2013.01); *A61K 9/7023* (2013.01); *A61K 31/565* (2013.01)

(58) Field of Classification Search
USPC .......................................... 514/169; 424/452
See application file for complete search history.

(56) References Cited

U.S. PATENT DOCUMENTS

| | | | |
|---|---|---|---|
| 2,232,438 A | 2/1941 | Butenandt | |
| 4,900,734 A * | 2/1990 | Maxson et al. | 514/171 |
| 5,538,736 A | 7/1996 | Hoffmann et al. | |
| 5,556,635 A | 9/1996 | Istin et al. | |
| 5,580,572 A | 12/1996 | Mikler et al. | |
| 5,605,702 A | 2/1997 | Teillaud et al. | |
| 5,607,691 A | 3/1997 | Hale et al. | |
| 5,607,693 A | 3/1997 | Bonte et al. | |
| 5,609,617 A | 3/1997 | Shealy et al. | |
| 5,626,866 A | 5/1997 | Ebert et al. | |
| 5,653,983 A | 8/1997 | Meybeck et al. | |
| 5,660,839 A | 8/1997 | Allec et al. | |
| 5,662,927 A | 9/1997 | Ehrlich et al. | |
| 5,663,160 A | 9/1997 | Meybeck et al. | |
| 5,686,097 A | 11/1997 | Taskovich et al. | |
| 5,693,335 A | 12/1997 | Xia et al. | |
| 5,700,480 A | 12/1997 | Hille et al. | |
| 5,719,197 A | 2/1998 | Kanios et al. | |
| 5,770,220 A | 6/1998 | Meconi et al. | |
| 5,770,227 A | 6/1998 | Dong et al. | |
| 5,780,044 A | 7/1998 | Yewey et al. | |
| 5,780,050 A | 7/1998 | Jain et al. | |
| 5,788,984 A | 8/1998 | Guenther et al. | |
| 5,820,878 A | 10/1998 | Hirano et al. | |
| 5,840,327 A | 11/1998 | Gale et al. | |
| 5,843,468 A | 12/1998 | Burkoth et al. | |
| 5,843,979 A | 12/1998 | Wille et al. | |
| 5,858,394 A | 1/1999 | Lipp et al. | |
| 5,863,552 A | 1/1999 | Yue | |
| 5,882,676 A | 3/1999 | Lee et al. | |
| 5,885,612 A | 3/1999 | Meconi et al. | |
| 5,888,533 A | 3/1999 | Dunn | |

(Continued)

FOREIGN PATENT DOCUMENTS

| | | |
|---|---|---|
| WO | WO9619975 | 7/1996 |
| WO | WO0241878 | 5/2002 |
| WO | WO03028667 | 4/2003 |
| WO | WO2004014432 | 2/2004 |
| WO | WO2005081825 | 9/2005 |
| WO | WO2007120868 | 10/2007 |
| WO | WO2010146872 | 12/2010 |
| WO | WO2012055814 A1 | 5/2012 |
| WO | WO2012055840 A1 | 5/2012 |
| WO | WO2012065740 | 5/2012 |

(Continued)

OTHER PUBLICATIONS

Abitec Corporation, Excipients for the Pharmaceutical Industry—Regulatory and Product Information, 2013, 2 pages.

(Continued)

*Primary Examiner* — Dennis J Parad
(74) *Attorney, Agent, or Firm* — Kilpatrick Townsend & Stockton; Marlan D. Walker

(57) ABSTRACT

Estrogen and progesterone replacement therapies are provided herein. Among others, the following formulations are provided herein: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone.

18 Claims, 4 Drawing Sheets

(56) References Cited

U.S. PATENT DOCUMENTS

| | | |
|---|---|---|
| 5,891,462 A | 4/1999 | Carrara |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,919,477 A | 7/1999 | Bevan et al. |
| 5,942,243 A | 8/1999 | Shah |
| 5,952,000 A | 9/1999 | Venkateshwaran et al. |
| 5,968,919 A | 10/1999 | Samour et al. |
| 5,985,311 A | 11/1999 | Cordes et al. |
| 5,985,850 A | 11/1999 | Falk et al. |
| 5,989,568 A | 11/1999 | Breton et al. |
| 6,007,835 A | 12/1999 | Bon Lapillonne et al. |
| 6,010,715 A | 1/2000 | Wick et al. |
| 6,013,276 A | 1/2000 | Math et al. |
| 6,024,974 A | 2/2000 | Li |
| 6,030,948 A | 2/2000 | Mann |
| 6,040,340 A | 3/2000 | Chwalisz et al. |
| 6,068,853 A | 5/2000 | Giannos et al. |
| 6,087,352 A | 7/2000 | Trout |
| 6,090,404 A | 7/2000 | Meconi et al. |
| 6,106,848 A | 8/2000 | Preuilh et al. |
| 6,124,362 A | 9/2000 | Bradbury et al. |
| 6,139,868 A | 10/2000 | Hoffmann |
| 6,149,935 A | 11/2000 | Chiang et al. |
| 6,187,323 B1 | 2/2001 | Aiache et al. |
| 6,217,886 B1 | 4/2001 | Onyuksel et al. |
| 6,225,297 B1 | 5/2001 | Stockemann et al. |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,267,984 B1 | 7/2001 | Beste et al. |
| 6,274,165 B1 | 8/2001 | Meconi et al. |
| 6,303,132 B1 | 10/2001 | Nelson |
| 6,303,588 B1 | 10/2001 | Danielov |
| 6,312,703 B1 | 11/2001 | Orthoefer |
| 6,328,987 B1 | 12/2001 | Marini |
| 6,344,211 B1 | 2/2002 | Hille |
| 6,372,245 B1 | 4/2002 | Bowman et al. |
| 6,420,352 B1 | 7/2002 | Knowles |
| 6,432,438 B1 | 8/2002 | Shukla |
| 6,451,300 B1 | 9/2002 | Dunlop et al. |
| 6,465,004 B1 | 10/2002 | Rossi Montero et al. |
| 6,465,005 B1 | 10/2002 | Biali et al. |
| 6,465,006 B1 | 10/2002 | Zhang et al. |
| 6,495,160 B2 | 12/2002 | Esposito et al. |
| 6,521,250 B2 | 2/2003 | Meconi et al. |
| 6,531,149 B1 | 3/2003 | Kirstgen et al. |
| 6,538,039 B2 | 3/2003 | Laurent |
| 6,548,053 B1 | 4/2003 | Stewart et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,599,519 B1 | 7/2003 | Seo et al. |
| 6,610,674 B1 | 8/2003 | Schreiber |
| 6,635,274 B1 | 10/2003 | Masiz et al. |
| 6,638,528 B1 | 10/2003 | Kanios |
| 6,649,155 B1 | 11/2003 | Dunlop et al. |
| 6,682,757 B1 | 1/2004 | Wright |
| 6,708,822 B1 | 3/2004 | Muni |
| 6,720,001 B2 | 4/2004 | Chen et al. |
| 6,743,448 B2 | 6/2004 | Kryger |
| 6,750,291 B2 | 6/2004 | Kim et al. |
| 6,821,524 B2 | 11/2004 | Marini |
| 6,911,211 B2 | 6/2005 | Eini et al. |
| 6,960,337 B2 | 11/2005 | Daniels et al. |
| 6,974,569 B2 | 12/2005 | Dunlop et al. |
| 6,995,149 B1 | 2/2006 | Endrikat et al. |
| 7,004,321 B1 | 2/2006 | Palm et al. |
| 7,030,104 B2 | 4/2006 | Gray et al. |
| 7,094,228 B2 | 8/2006 | Zhang et al. |
| 7,097,853 B1 | 8/2006 | Garbe et al. |
| 7,105,573 B2 | 9/2006 | Krajcik et al. |
| 7,153,522 B1 | 12/2006 | Ikeura et al. |
| 7,175,850 B2 | 2/2007 | Cevc |
| 7,198,800 B1 | 4/2007 | Ko |
| 7,381,427 B2 | 6/2008 | Ancira et al. |
| 7,456,159 B2 | 11/2008 | Houze et al. |
| 7,498,303 B2 | 3/2009 | Arnold et al. |
| 7,534,780 B2 | 5/2009 | Wyrwa et al. |
| 7,569,274 B2 | 8/2009 | Besse et al. |
| 7,799,769 B2 | 9/2010 | White et al. |
| 7,815,936 B2 | 10/2010 | Hasenzahl et al. |
| 7,829,116 B2 | 11/2010 | Griswold et al. |
| 7,850,992 B2 | 12/2010 | Kim et al. |
| 7,854,753 B2 | 12/2010 | Kraft et al. |
| 7,871,643 B2 | 1/2011 | Lizio et al. |
| 7,960,368 B2 | 6/2011 | Nickisch et al. |
| 8,048,017 B2 | 11/2011 | Xu |
| 8,063,030 B2 | 11/2011 | Ellman |
| 8,071,576 B2 | 12/2011 | Coelingh Bennink et al. |
| 8,075,916 B2 | 12/2011 | Song et al. |
| 8,075,917 B2 | 12/2011 | Chung et al. |
| 8,076,317 B2 | 12/2011 | Kulmann |
| 8,080,553 B2 | 12/2011 | Keith et al. |
| 8,096,940 B2 | 1/2012 | Josephson et al. |
| 8,114,152 B2 | 2/2012 | Furst |
| 8,114,442 B2 | 2/2012 | Tucker et al. |
| 8,119,741 B2 | 2/2012 | Pavlin |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,163,722 B2 | 4/2012 | Savoir et al. |
| 8,177,449 B2 | 5/2012 | Bayly et al. |
| 8,187,615 B2 | 5/2012 | Friedman |
| 8,195,403 B2 | 6/2012 | Ishikawa et al. |
| 8,221,785 B2 | 7/2012 | Chien |
| 8,222,237 B2 | 7/2012 | Nickisch et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,337,814 B2 | 12/2012 | Osbakken et al. |
| 8,344,007 B2 | 1/2013 | Tang et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Boehler et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,415,332 B2 | 4/2013 | Diliberti et al. |
| 8,435,972 B2 | 5/2013 | Stein et al. |
| 8,449,879 B2 | 5/2013 | Laurent Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Barrett et al. |
| 8,541,400 B2 | 9/2013 | Johnsson et al. |
| 8,551,462 B2 | 10/2013 | Goldstein et al. |
| 8,557,281 B2 | 10/2013 | Halliday et al. |
| 8,568,374 B2 | 10/2013 | De Graaff et al. |
| 8,591,951 B2 | 11/2013 | Kohn et al. |

(56) References Cited

U.S. PATENT DOCUMENTS

| | | |
|---|---|---|
| 8,613,951 B2 | 12/2013 | Zale et al. |
| 8,633,178 B2 | 1/2014 | Bernick et al. |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Nam et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmuller Nethl et al. |
| 8,784,882 B2 | 7/2014 | Mattern |
| 2001/0009673 A1 | 7/2001 | Lipp et al. |
| 2001/0023261 A1 | 9/2001 | Ryoo et al. |
| 2001/0053383 A1 | 12/2001 | Miranda et al. |
| 2002/0035070 A1 | 3/2002 | Gardlik et al. |
| 2002/0119174 A1 | 8/2002 | Gardlik et al. |
| 2002/0119198 A1 | 8/2002 | Gao et al. |
| 2002/0142017 A1 | 10/2002 | Simonnet |
| 2002/0169205 A1 | 11/2002 | Chwalisz et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0027772 A1 | 2/2003 | Breton |
| 2003/0044453 A1 | 3/2003 | Dittgen et al. |
| 2003/0091620 A1 | 5/2003 | Fikstad et al. |
| 2003/0109507 A1 | 6/2003 | Franke et al. |
| 2003/0113268 A1 | 6/2003 | Buenafae et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0219402 A1 | 11/2003 | Rutter |
| 2003/0225047 A1 | 12/2003 | Caubel et al. |
| 2003/0225048 A1 | 12/2003 | Caubel et al. |
| 2003/0235596 A1 | 12/2003 | Gao et al. |
| 2003/0236236 A1 | 12/2003 | Chen et al. |
| 2004/0022820 A1 | 2/2004 | Anderson |
| 2004/0039356 A1 | 2/2004 | Maki et al. |
| 2004/0043043 A1 | 3/2004 | Schlyter et al. |
| 2004/0048900 A1 | 3/2004 | Flood |
| 2004/0087564 A1 | 5/2004 | Wright et al. |
| 2004/0092494 A9 | 5/2004 | Dudley |
| 2004/0110732 A1 | 6/2004 | Masini Eteve et al. |
| 2004/0138103 A1 | 7/2004 | Patt |
| 2004/0146539 A1 | 7/2004 | Gupta |
| 2004/0161435 A1 | 8/2004 | Gupta |
| 2004/0191207 A1 | 9/2004 | Lipari et al. |
| 2004/0210280 A1 | 10/2004 | Liedtke |
| 2004/0219124 A1 | 11/2004 | Gupta |
| 2004/0225140 A1 | 11/2004 | Fernandez et al. |
| 2004/0241219 A1 | 12/2004 | Hille et al. |
| 2005/0003003 A1 | 1/2005 | Basu et al. |
| 2005/0014729 A1 | 1/2005 | Pulaski |
| 2005/0020550 A1 | 1/2005 | Morris et al. |
| 2005/0054991 A1 | 3/2005 | Tobyn et al. |
| 2005/0118244 A1 | 6/2005 | Theobald et al. |
| 2005/0129756 A1 | 6/2005 | Podhaisky et al. |
| 2005/0152956 A1 | 7/2005 | Dudley |
| 2005/0186141 A1 | 8/2005 | Gonda et al. |
| 2005/0196434 A1 | 9/2005 | Brierre |
| 2005/0220900 A1 | 10/2005 | Popp et al. |
| 2005/0239747 A1 | 10/2005 | Yang et al. |
| 2005/0239758 A1 | 10/2005 | Roby |
| 2005/0244360 A1 | 11/2005 | Billoni |
| 2005/0266088 A1 | 12/2005 | Hinrichs et al. |
| 2005/0271597 A1 | 12/2005 | Keith |
| 2005/0272685 A1 | 12/2005 | Hung |
| 2006/0009428 A1 | 1/2006 | Grubb et al. |
| 2006/0034904 A1 | 2/2006 | Weimann |
| 2006/0078618 A1 | 4/2006 | Constantinides et al. |
| 2006/0084704 A1 | 4/2006 | Shih et al. |
| 2006/0088580 A1 | 4/2006 | Meconi et al. |
| 2006/0100180 A1 | 5/2006 | Nubbemeyer et al. |
| 2006/0121102 A1 | 6/2006 | Chiang |
| 2006/0165744 A1 | 7/2006 | Jamil et al. |
| 2006/0193789 A1 | 8/2006 | Tamarkin et al. |
| 2006/0233743 A1 | 10/2006 | Kelly |
| 2006/0233841 A1 | 10/2006 | Brodbeck et al. |
| 2006/0246122 A1 | 11/2006 | Langguth et al. |
| 2006/0247221 A1 | 11/2006 | Coelingh Bennink et al. |
| 2006/0251581 A1 | 11/2006 | McIntyre et al. |
| 2006/0275218 A1 | 12/2006 | Tamarkin et al. |
| 2006/0276414 A1 | 12/2006 | Coelingh Bennink et al. |
| 2006/0292223 A1 | 12/2006 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |
| 2007/0037780 A1 | 2/2007 | Ebert et al. |
| 2007/0037782 A1 | 2/2007 | Hibino et al. |
| 2007/0078091 A1 | 4/2007 | Hubler et al. |
| 2007/0128263 A1 | 6/2007 | Gargiulo et al. |
| 2007/0154533 A1 | 7/2007 | Dudley |
| 2007/0167418 A1 | 7/2007 | Ferguson |
| 2007/0185068 A1 | 8/2007 | Ferguson et al. |
| 2007/0190022 A1 | 8/2007 | Bacopoulos et al. |
| 2007/0196415 A1 | 8/2007 | Chen et al. |
| 2007/0232574 A1 | 10/2007 | Galey et al. |
| 2007/0248658 A1 | 10/2007 | Zurdo Schroeder et al. |
| 2007/0254858 A1 | 11/2007 | Cronk |
| 2007/0255197 A1 | 11/2007 | Humberstone et al. |
| 2007/0287688 A1 | 12/2007 | Chan et al. |
| 2007/0292359 A1 | 12/2007 | Friedman et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026040 A1 | 1/2008 | Farr et al. |
| 2008/0038219 A1 | 2/2008 | Mosbaugh et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0095831 A1 | 4/2008 | McGraw |
| 2008/0138390 A1 | 6/2008 | Hsu et al. |
| 2008/0139392 A1 | 6/2008 | Acosta Zara et al. |
| 2008/0153789 A1 | 6/2008 | Dmowski et al. |
| 2008/0175905 A1 | 7/2008 | Liu et al. |
| 2008/0175908 A1 | 7/2008 | Liu et al. |
| 2008/0206156 A1 | 8/2008 | Cronk |
| 2008/0206159 A1 | 8/2008 | Tamarkin et al. |
| 2008/0214512 A1 | 9/2008 | Seitz et al. |
| 2008/0226698 A1 | 9/2008 | Tang et al. |
| 2008/0227763 A1 | 9/2008 | Lanquetin et al. |
| 2008/0234240 A1 | 9/2008 | Duesterberg et al. |
| 2008/0261931 A1 | 10/2008 | Hedner et al. |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0060997 A1 | 3/2009 | Seitz et al. |
| 2009/0081206 A1 | 3/2009 | Leibovitz |
| 2009/0093440 A1 | 4/2009 | Murad |
| 2009/0098069 A1 | 4/2009 | Vacca |
| 2009/0099149 A1 | 4/2009 | Liu et al. |
| 2009/0130029 A1 | 5/2009 | Tamarkin et al. |

(56) References Cited

U.S. PATENT DOCUMENTS

| | | |
|---|---|---|
| 2009/0175799 A1 | 7/2009 | Tamarkin et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0227550 A1 | 9/2009 | Mattern |
| 2009/0285869 A1 | 11/2009 | Trimble |
| 2009/0324714 A1 | 12/2009 | Liu et al. |
| 2010/0008985 A1 | 1/2010 | Pellikaan et al. |
| 2010/0034838 A1 | 2/2010 | Staniforth et al. |
| 2010/0034880 A1 | 2/2010 | Sintov et al. |
| 2010/0055138 A1 | 3/2010 | Margulies et al. |
| 2010/0086501 A1 | 4/2010 | Chang et al. |
| 2010/0119585 A1 | 5/2010 | Hille et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0204326 A1 | 8/2010 | D Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0247482 A1 | 9/2010 | Cui et al. |
| 2010/0247635 A1 | 9/2010 | Rosenberg et al. |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0322884 A1 | 12/2010 | Dipietro et al. |
| 2011/0039814 A1 | 2/2011 | Huatan et al. |
| 2011/0087192 A1 | 4/2011 | Uhland et al. |
| 2011/0098258 A1 | 4/2011 | Masini Eteve et al. |
| 2011/0104268 A1 | 5/2011 | Pachot et al. |
| 2011/0130372 A1 | 6/2011 | Agostinacchio et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0190201 A1 | 8/2011 | Hyde et al. |
| 2011/0195031 A1 | 8/2011 | Du |
| 2011/0238003 A1 | 9/2011 | Bruno Raimondi et al. |
| 2011/0244043 A1 | 10/2011 | Xu et al. |
| 2011/0250256 A1 | 10/2011 | Hyun Oh et al. |
| 2011/0250259 A1 | 10/2011 | Buckman |
| 2011/0262373 A1 | 10/2011 | Umbert Millet |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0318405 A1 | 12/2011 | Erwin |
| 2011/0318431 A1 | 12/2011 | Gulati |
| 2012/0021041 A1 | 1/2012 | Rossi et al. |
| 2012/0028888 A1 | 2/2012 | Janz et al. |
| 2012/0028910 A1 | 2/2012 | Combal et al. |
| 2012/0028936 A1 | 2/2012 | Gloger et al. |
| 2012/0046264 A1 | 2/2012 | Simes et al. |
| 2012/0046518 A1 | 2/2012 | Yoakum et al. |
| 2012/0058171 A1 | 3/2012 | De Graaff et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0172343 A1 | 7/2012 | Lindenthal et al. |
| 2012/0184515 A1 | 7/2012 | Klar et al. |
| 2012/0231052 A1 | 9/2012 | Sitruk Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0277249 A1 | 11/2012 | Andersson et al. |
| 2012/0277727 A1 | 11/2012 | Doshi et al. |
| 2012/0295911 A1 | 11/2012 | Mannion et al. |
| 2012/0301517 A1 | 11/2012 | Zhang et al. |
| 2012/0301538 A1 | 11/2012 | Gordon Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot Petit et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029957 A1 | 1/2013 | Giliyar et al. |
| 2013/0045266 A1 | 2/2013 | Choi et al. |
| 2013/0045953 A1 | 2/2013 | Sitruk Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0131027 A1 | 5/2013 | Pakkalin et al. |
| 2013/0131028 A1 | 5/2013 | Snyder et al. |
| 2013/0131029 A1 | 5/2013 | Bakker et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0210709 A1 | 8/2013 | McMurry et al. |
| 2013/0216550 A1 | 8/2013 | Penninger et al. |
| 2013/0216596 A1 | 8/2013 | Viladot Petit et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari Lodriche et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da Silva Maia Filho |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |

(56) References Cited

U.S. PATENT DOCUMENTS

| | | |
|---|---|---|
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338124 A1 | 12/2013 | Li et al. |
| 2013/0345187 A1 | 12/2013 | Rodriguez Oquendo |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Barman et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0100159 A1 | 4/2014 | Conrad |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |

FOREIGN PATENT DOCUMENTS

| | | |
|---|---|---|
| WO | WO2012098090 A1 | 7/2012 |
| WO | WO2012116277 A1 | 8/2012 |
| WO | WO2012118563 A2 | 9/2012 |
| WO | WO2012120365 A1 | 9/2012 |
| WO | WO2012127501 A2 | 9/2012 |
| WO | WO2012156561 A1 | 11/2012 |
| WO | WO2012156822 A1 | 11/2012 |
| WO | WO2012158483 A2 | 11/2012 |
| WO | WO2012166909 A1 | 12/2012 |
| WO | WO2012170578 A1 | 12/2012 |
| WO | WO2013011501 A1 | 1/2013 |
| WO | WO2013025449 A1 | 2/2013 |
| WO | WO2013028639 A1 | 2/2013 |
| WO | WO2013035101 A1 | 3/2013 |
| WO | WO2013044067 A1 | 3/2013 |
| WO | WO2013045404 A2 | 4/2013 |
| WO | WO2013059285 A1 | 4/2013 |
| WO | WO2013063279 A1 | 5/2013 |
| WO | WO2013064620 A1 | 5/2013 |
| WO | WO2013071281 A1 | 5/2013 |
| WO | WO2013088254 | 6/2013 |
| WO | WO2013102665 A1 | 7/2013 |
| WO | WO2013106437 A1 | 7/2013 |
| WO | WO2013113690 | 8/2013 |
| WO | WO2013124415 A1 | 8/2013 |
| WO | WO2013127727 A1 | 9/2013 |
| WO | WO2013127728 A1 | 9/2013 |
| WO | WO2013144356 A1 | 10/2013 |
| WO | WO2013149258 A2 | 10/2013 |
| WO | WO2013158424 A2 | 10/2013 |
| WO | WO2013158454 A2 | 10/2013 |
| WO | WO2013170052 A1 | 11/2013 |
| WO | WO2013178587 A1 | 12/2013 |
| WO | WO2013181449 A1 | 12/2013 |
| WO | WO2014001904 A1 | 1/2014 |
| WO | WO2014004424 A1 | 1/2014 |
| WO | WO2014009434 A1 | 1/2014 |
| WO | WO2014018569 A1 | 1/2014 |
| WO | WO2014018570 A1 | 1/2014 |
| WO | WO2014018571 A2 | 1/2014 |
| WO | WO2014018856 A1 | 1/2014 |
| WO | WO2014018932 A2 | 1/2014 |
| WO | WO2014031958 A1 | 2/2014 |
| WO | WO2014041120 A1 | 3/2014 |
| WO | WO2014052792 A1 | 4/2014 |
| WO | WO2014056897 A1 | 4/2014 |
| WO | WO2014066442 A2 | 5/2014 |
| WO | WO2014074846 A1 | 5/2014 |
| WO | WO2014076231 A1 | 5/2014 |
| WO | WO2014076569 A2 | 5/2014 |
| WO | WO2014081598 A1 | 5/2014 |
| WO | WO2014086739 A1 | 6/2014 |
| WO | WO2014093114 A1 | 6/2014 |
| WO | WO2014104784 A1 | 7/2014 |

OTHER PUBLICATIONS

Corbett et al., "Trends in Pharmacy Compounding for Women's Health in North Carolina: Focus on Vulvodynia," Southern Medical Journal, vol. 107, No. 7, Jul. 2014, pp. 433-436.

Shrier et al., "Mucosal Immunity of the Adolescent Female Genital Tract," Journal of Adolescent Health, 2003; 32:183-186.

Gattefossé Sas, Material Safety Data Sheet, Gelot 64, 2012, 8 pages.

Gattefossé Sas, Regulatory Data Sheet, Gelot 64, 2012, 6 pages.

Gattefossé Sas, Regulatory Data Sheet, Lauroglycol 90, 2012, 5 pages.

Hatton et al., "Safety and efficacy of a lipid emulsion containing medium-chain triglycerides," Clinical Pharmacy, 1990, vol. 9, No. 5, pp. 366-371.

Lauer et al., "Evaluation of the hairless rat as a model for in vivo percutaneous absorption," Journal of Pharmaceutical Sciences, vol. 86, No. 1, Jan. 1997, pp. 13-18.

Sasol Olefins & Surfactants GmbH, Excipients for Pharmaceuticals, 2010, 28 pages.

Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.

Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.

ZRT Laboratory, Provider Data Sheet, About Dried Blood Spot Testing, 2014, 3 pages.

\* cited by examiner

NATURAL COMBINATION HORMONE REPLACEMENT FORMULATIONS AND THERAPIES

CROSS-REFERENCES TO RELATED APPLICATIONS

This application is a continuation of U.S. patent application Ser. No. 14/099,545, entitled "NATURAL COMBINATION HORMONE REPLACEMENT FORMULATIONS AND THERAPIES" which was filed on Dec. 6, 2013, which application is a divisional of U.S. patent application Ser. No. 13/684,002, entitled "NATURAL COMBINATION HORMONE REPLACEMENT FORMULATIONS AND THERAPIES" which was filed on Nov. 21, 2012 (now U.S. Pat. No. 8,633,178, issued Jan. 21, 2014), which application claims priority to the following U.S. Provisional Patent Applications: U.S. Provisional Application Ser. No. 61/563,408, entitled "NATURAL COMBINATION HORMONE REPLACEMENT THERAPIES" which was filed on Nov. 23, 2011; U.S. Provisional Application Ser. No. 61/661,302, entitled "ESTRADIOL FORMULATIONS" which was filed on Jun. 18, 2012; and U.S. Provisional Application Ser. No. 61/662,265, entitled "PROGESTERONE FORMULATIONS" which was filed on Jun. 20, 2012. All aforementioned applications are hereby incorporated by reference herein in their entirety.

FIELD OF THE INVENTION

This disclosure relates to natural estrogen and progesterone replacement therapies, with formulations provided for each estradiol and progesterone alone and in combination for the treatment of pre, peri-menopausal, menopausal and post-menopausal females in relation to the treatment of Estrogen- and Progesterone-deficient States, each as herein below defined.

BACKGROUND OF THE INVENTION

Hormone replacement therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones regardless as to whether the subject is pre-menopausal, peri-menopausal, menopausal or post-menopausal. However, specific disease states can exist during each stage of menopausal progression.

HRT is presently available in various forms. One therapy involves administration of low dosages of one or more estrogens. Another involves administration of progesterone or a chemical analogue, called a progestin. Progesterone administration acts, among treating other disease states, to mitigate certain undesirable side effects from estrogen administration including, for example, endometrial hyperplasia (thickening), reducing the incidence of endometrial cancer.

Timing for dosage administration is often varied cyclically, with estrogens taken daily and progesterone taken for approximately two weeks of every month; a method often referred to as "Cyclic-Sequential" or "Sequentially-Combined HRT." This method is intended to mimic the natural menstrual cycle and typically causes menstruation similar to a period after the progesterone is stopped. This regimen is most typically used in peri-menopausal or newly menopausal women as the alternative continuous method often results in irregular bleeding in such women. An alternate method, a constant dosage with both estrogen and progesterone taken daily, is called "continuous-combined HRT." This method usually results in no menstruation and is used most often after a woman has been menopausal for some time.

Estrogen, in its various forms, and progesterone, in its various forms, are used in HRT via a variety of administered dosage forms including, for example, via tablets, capsules and patches.

"Bio-identical" hormones, which are identical in chemical structure to the hormones naturally produced by human bodies can be used and are often referred to as natural hormone replacement therapy, or NHRT.

These natural or bio-identical hormones are formulated from various ingredients to match the chemical structure and effect of estradiol, estrone, or estriol (the 3 primary estrogens) as well as progesterone that occur naturally in the human body (endogenous).

Currently, bio-identical estradiol is available in both branded and generic FDA approved versions. FDA-approved bio-identical progesterone for HRT is available as the branded stand-alone drug commercially identified as Prometrium® (Abbott Laboratories, Abbott Park, Ill.), with a generic authorized by the innovator, and generic products provided by Teva (Israel) and Sofgen Americas, Inc (New York). Other products such as Prempro® and Premphase® (Wyeth Laboratories, a division Pfizer, Inc., New York) provide both continuous-combined and cyclic-sequential products containing Premarin (estrogen derived from mare's urine) and synthetic medroxyprogesterone acetate. Other products are available. However, no FDA approved product exists on the market today with combination bio-identical estradiol and bio-identical progesterone.

SUMMARY OF THE INVENTION

According to various embodiments of the disclosure, natural hormone replacement therapies are provided comprising cyclic/sequential and continuous-combined delivery via pharmaceutical formulations of solubilized estradiol and micronized and/or partially or completely solubilized progesterone. Estradiol and micronized and/or partially or completely solubilized progesterone delivered together daily can be combined in either a single unit dose or in separate unit doses, typically in a soft capsule. A 28-day or monthly regimen of tablets or capsules can be packaged in a single blister pack having delivery days identified to improve compliance. Various examples formulations of natural hormones, and the use of these formulations for hormone replacement therapies, each in accordance with the invention are set forth below.

BRIEF DESCRIPTION OF THE DRAWINGS

The accompanying drawings, which are incorporated herein and form a part of the specification, illustrate the present disclosure and, together with the description, further serve to explain the principles of the disclosure and to enable a person skilled in the pertinent art to make and use the disclosed embodiments.

DETAILED DESCRIPTION OF THE INVENTION

Figure 1:
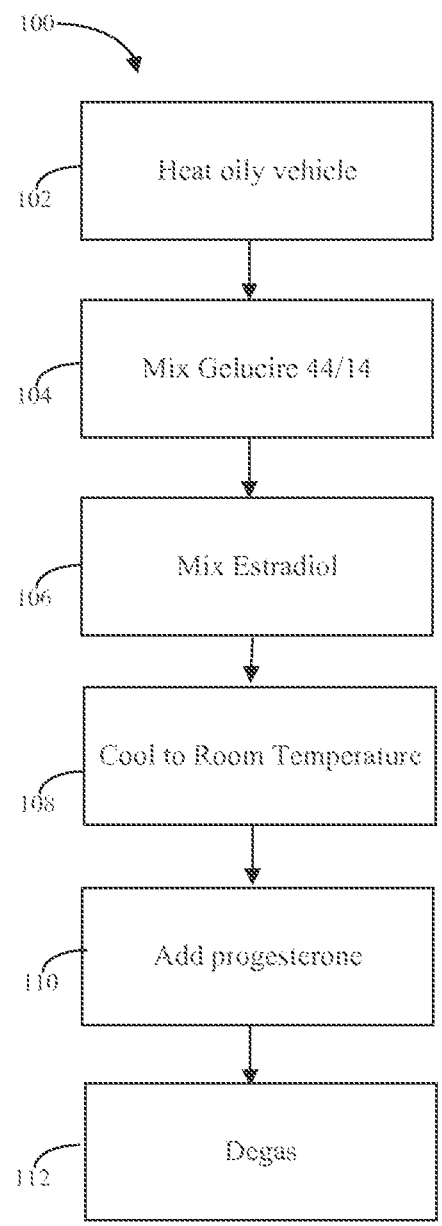
FIG. 1 illustrates an exemplary manufacturing process of a fill material in accordance with various embodiments.

Frequently, higher recommended oral dosages of pharmaceuticals are necessary to treat a given disease state because many active ingredients are not completely absorbed by a patient in need of treatment. In other words, a better-absorbed dosage form of a medicament such as, for example, progesterone, or dosage forms that provide greater consistency of absorption of progesterone among subjects, alone or in combination with estradiol, may be able to be administered at dosage strengths lower than presently recommended, potentially resulting in a reduced or minimized side effect profile, among other potential benefits.

A. DEFINITIONS

The term "micronized progesterone," as used herein, includes micronized progesterone having an X50 particle size value below about 15 microns and/or having an X90 particle size value below about 25 microns.

The term "X50," as used herein, means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "medium chain," as used herein means any medium chain carbon-containing substance, including C4-C18, and including C6-C12 substances, fatty acid esters of glycerol, fatty acids, and mono-, di-, and tri-glycerides of such substances.

The term "uniform distribution" means at least one of uniform dispersion, solubility, or lack of agglomeration of progesterone in a dissolution test compared to Prometrium at a similar dosage strength and the same USP dissolution apparatus.

The term "bioavailability," as used herein means the concentration of an active ingredient (e.g., progesterone or estradiol or estrone) in the blood (serum or plasma). The relative bioavailability may be measured as the concentration in the blood (serum or plasma) versus time. Other pharmacokinetic (pK) indicators may be used to measure and assess bioavailability, determined by suitable metrics including AUC, $C_{max}$, and optionally, Tmax.

The term "AUC," as used herein, refers to the area under the curve that represents changes in blood concentration of progesterone, estradiol or estrone over time.

The term, "$C_{max}$" as used herein, refers to the maximum value of blood concentration shown on the curve that represents changes in blood concentrations of progesterone, estradiol or estrone over time.

The term, "$T_{max}$" as used herein, refers to the time that it takes for progesterone, estradiol or estrone blood concentration to reach the maximum value.

Collectively AUC, $C_{max}$ and, optionally, $T_{max}$ are the principle pharmacokinetic parameters that can characterize the pharmacokinetic responses of a particular drug product such as progesterone in an animal or human subject.

The term "solubilizer," as used herein, means any substance or mixture of substances that may be used to enhance the solubility of estradiol, including, for example and without limitation, appropriate pharmaceutically acceptable excipients, such as solvents, co-solvents, surfactants, emulsifiers, oils and carriers.

The term "excipients," as used herein, refer to non-active pharmaceutical ingredients ("API") substances such as carriers, solvents, oils, lubricants and others used in formulating pharmaceutical products. They are generally safe for administering to animals, including humans, according to established governmental standards, including those promulgated by the United States Food and Drug Administration.

The term "oil" as used herein may be any pharmaceutically acceptable substance, other than peanut oil, that would suspend and/or solubilize any suitable progesterone, starting material, or precursor, including micronized progesterone as described herein. More specifically, oils may include, for example and without limitation, medium chain fatty acids, generally of the group known as medium chain fatty acids consisting of at least one mono-, di-, and triglyceride, or derivatives thereof, or combinations thereof.

"Fully solubilized progesterone" as used herein means progesterone which is about 100% in solution.

"Partially solubilized progesterone" as used herein means progesterone which is in any state of solubilization up to but not including about 100%.

B. DESCRIPTION AND PREFERRED EMBODIMENTS

Provided herein are the following formulations: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone. The underlying formulation concepts provided herein may be used with other natural or synthetic forms of estradiol and progesterone. Micronization specifications, aspects and embodiments are further defined herein.

Generally, the pharmaceutical formulations described herein are prepared and administered as filled capsules, typically soft capsules of one or more materials well known in the art including, for example and without limitation, soft gelatin capsules. Micronized progesterone, as described herein, may also be prepared for administration in tablets or other well-known orally administered dosage forms using standard techniques.

Another aspect of the present disclosure includes a pharmaceutical formulation of micronized progesterone, micronized progesterone with partially solubilized progesterone and fully solubilized progesterone, wherein said formulation may provide increased progesterone bioavailability in a treated subject compared to the bioavailability provided by Prometrium® when administered at equal dosage strengths.

In accordance with various aspects and embodiments, the solubility proportion (i.e., the proportion of a solute that enters solution) is notable. The weight ratio of estradiol to the weight of the entire solution is also notable due to the intended dose amounts, discussed herein. In particular, it is desirable to obtain a target dosage of estradiol in an amount of solution that may be readily administered via a capsule. For example, if it is desired to have a dose of estradiol in a capsule of between about 0.125 mg to about 2 mg, it would also be desirable to have a total solution weight to be between about 250 mg to about 400 mg, preferably about 300 mg to about 350 mg and more preferably about 325 mg. In various embodiments, the following weight ratios of estradiol to total solution is from about 0.125/50 mg to about 0.125/1000 mg, from about 1 mg:500 mg to about 1 mg:50 mg; from about 1 mg:250 mg to about 1 mg:60 mg; from about 1 mg:100 mg to about 1 mg:66 mg; from about 2 mg/50 mg to about 2 mg/1000 mg. In various embodiments, the target for single dose product is 325 mg, and a target fill weight for a combination product (e.g., two or more sterol APIs) is 650 mg.

Other aspects of the present disclosure further provide: more uniform dissolution of progesterone, and reduced intra- and inter-patient blood level variability in formulations of progesterone of the present disclosure, typically in combinations with solubilized estradiol, when compared to equal dosages of Prometrium. Blood level variability is also compared at equal sampling times following administration. Not to be limited by theory, these aspects are believed to be influenced by the percentage of solubilized progesterone in a respective formulation wherein such more uniform dissolution of progesterone, and lower intra- and inter-patient blood level variability, are influenced by a greater proportion of solubilized progesterone relative to total progesterone. A reduced food effect with the present formulations comprising progesterone may also be implicated.

More uniform dissolution of progesterone in a formulation of the present disclosure compared to the dissolution of Prometrium at equal dosage strengths and using the same USP apparatus can be determined using standard techniques established for API dissolution testing, including that which is described in the examples below.

Reduced intra- and inter-patient variability of progesterone formulated pursuant to the present disclosure compared to Prometrium can be demonstrated via a fed bio-study such as that described below.

Other aspects of the present disclosure includes the use of formulations as described herein wherein progesterone is at least one API in said formulation for the treatment of an animal, including humans: for endometrial hyperplasia; for secondary amenorrhea; as a method of treatment for preterm birth, when said animal has a shortened cervix, and other disease states or conditions treated with supplemental progesterone (collectively, "Progesterone-deficient States"); and the use of formulations as described herein wherein estradiol is at least one API in said formulation for the treatment of an animal, including humans, having menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvo-vaginal atrophy; and osteoporosis and other non-menopausal disease states or conditions treated with supplemental estrogen. (collectively, "Estrogen-deficient States"), each in a subject in need of treatment, and each with a non-toxic effective amount of said formulations. As used herein, the term "treatment", or a derivative thereof, contemplates partial or complete inhibition of the stated disease state when a formulation as described herein is administered prophylactically or following the onset of the disease state for which such formulation is administered. For the purposes of the present disclosure, "prophylaxis" refers to administration of the active ingredient(s) to an animal to protect the animal from any of the disorders set forth herein, as well as others.

Unless otherwise specified, "natural," as used herein with reference to hormones discussed herein, means bio-identical hormones formulated to match the chemical structure and effect of those that occur naturally in the human body (endogenous). An exemplary natural estrogen is estradiol (also described as 17β-estradiol and E2) and a natural progestin is progesterone. An exemplary cyclic/sequential regimen comprises delivery of from about 0.125 mg to about 2.0 mg of estradiol daily for 14-18 days, followed by delivery of from about 0.125 mg to about 2 mg of estradiol and about 25 mg to about 200 mg of progesterone daily for 10-14 days. Cyclic/sequential regimens may be especially useful for menopausal females. Other exemplary dosage strengths for estradiol for use in the formulations described herein include, without limitation, 0.125, 0.25, 0.375, 0.50, 0.625, 0.75, 1.00, 1.125, 1.25, 1.375, 1.50, 1.625, 1.75 and 2.00 mg. Other exemplary dosage strengths for progesterone for use in the formulations described herein include, without limitation, 25, 50, 75, 100, 125, 150, 175, 200 mg, 250 mg, 300 mg, 350 mg and 400 mg. These dosage strengths for each of estradiol and progesterone can be administered in formulations described herein either alone or in combination.

Progesterone active pharmaceutical ingredient may be micronized via any one of the multiple methods typically utilized by the ordinarily skilled artisan. In various embodiments, micronized progesterone has an X50 particle size value of less than about 15 microns, less than about 10 microns, less than about 5 microns and/or less than about 3 microns. In various embodiments, micronized progesterone has an X90 particle size value of less than about 25 microns, less than about 20 microns, and/or less than about 15 microns.

Particle size may be determined in any suitable manner. For example, a Beckman Coulter LS 13 320 Laser Diffraction Particle Size Analyzer (the "Beckman Device") may be used to determine particle size. As described above, particle size may be represented by various metrics, for example, through an X50 particle size, and/or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 μm to 2000 μm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, and/or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 μm to 2000 μm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

Each of estradiol and progesterone as described herein can be formulated alone pursuant to the teachings below. These formulations can be prepared for oral administration or can be combined, based on compatibility, for co-administration of estradiol and progesterone in a single oral unit dosage form.

Progesterone formulations of the present disclosure are prepared via blending with a pharmaceutically acceptable oil; generally, the oil comprises at least one medium chain fatty acid such as medium chain fatty acids consisting of at least one mono-, di-, or triglyceride, or derivatives thereof, or combinations thereof. Optionally added are other excipients including, for example and without limitation, anti-oxidants, lubricants and the like. Sufficient oil is used to form a suspension of micronized progesterone or, in the alternative, solubilize progesterone.

Pharmaceutically acceptable oils include, without limitation, the use of at least one of a caproic fatty acid; a caprylic fatty acid; a capric fatty acid; a tauric acid; a myristic acid; a linoleic acid; a succinic acid; a glycerin; mono-, di-, or trig-lycerides and combinations and derivatives thereof; a polyethylene glycol; a polyethylene glycol glyceride (Gelucire®; GATTEFOSSE SAS, Saint-Priest, France); a propylene glycol; a caprylic/capric triglyceride (Miglyol®; SASOL Germany GMBH, Hamburg; Miglyol includes Miglyol 810, 812, 816 and 829); a caproic/caprylic/capric/lauric triglyceride; a caprylic/capric/linoleic triglyceride; a caprylic/capric/succinic triglyceride; a propylene glycol monocaprylate; propylene glycol monocaprate; (Capmul® PG-8 and 10; the Capmul brands are owned by ABITEC, Columbus Ohio); a propylene glycol dicaprylate; a propylene glycol dicaprylate; medium chain mono- and di-glycerides (Capmul MCM); a diethylene glycol mono ester (including 2-(2-Ethoxyethoxy) ethanol: Transcutol); a diethylene glycol monoethyl; esters of saturated coconut and palm kernel oil and derivatives thereof; triglycerides of fractionated vegetable fatty acids, and combinations and derivatives thereof.

In other aspects and embodiments, progesterone is fully solubilized using, for example and without limitation, sufficient amounts of: Transcutol and Miglyol; Transcutol, Miglyol and Capmul PG 8 and/or PG 10; Campul MCM; Capmul MCM and a non-ionic surfactant; and Campul MCM and Gelucire.

Various ratios of these oils can be used for full solubilization of progesterone. Capmul MCM and a non-ionic surfactant can be used at ratios including, for example and without limitation: 65:35, 70:30, 75:25, 80:20, 85:15 and 90:10. Campul MCM and Gelucire can be used at ratios including, for example and without limitation, 6:4, 7:3, 8:2, and 9:1. Among other combinations, these oils and/or solubilizers, as defined herein, and combinations thereof, can be used to form combination estradiol and progesterone formulations of the present disclosure.

Combinations of these oils can produce partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In various embodiments, estradiol is partially, substantially or completely solubilized. Solubilized estradiol may include estradiol that is approximately: 90% soluble in a solvent; 93% soluble in a solvent; 95% soluble in a solvent; 97% soluble in a solvent; 99% soluble in a solvent; and 100% soluble in a solvent. Solubility may be expressed as a mass fraction (% w/w).

In various embodiments, the solubilizing agent is selected from at least one of a solvent or co-solvent. Suitable solvents and co-solvents include any mono-, di- or triglyceride and glycols, and combinations thereof.

In addition to the oils referenced above for progesterone, which can also be used as solubilizers for estradiol, other solubilizers include, for example and without limitation, glyceryl mono- and di-caprylates, propylene glycol and 1,2, 3-propanetriol (glycerol, glycerin, glycerine).

Anionic and/or non-ionic surfactants can be used in other embodiments of the presently disclosed formulations containing estradiol, progesterone or a combination thereof. In certain embodiments, a non-ionic surfactant is used. Exemplary non-ionic surfactants may include, for example and without limitation, one or more of oleic acid, linoleic acid, palmitic acid, and stearic acid. In further embodiments, the non-ionic surfactant may comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass.

In various other embodiments, the non-ionic surfactant is selected from one or more of glycerol and polyethylene glycol esters of long chain fatty acids, for example, lauroyl macrogol-32 glycerides and/or lauroyl polyoxyl-32 glycerides, commercially available as Gelucire, including, for example, Gelucire 44/11 and Gelucire 44/14. These surfactants may be used at concentrations greater than about 0.01%, and typically in various amounts of about 0.01%-10.0%, 10.1%-20%, and 20.1%-30%.

In other embodiments, a lubricant is used. Any suitable lubricant may be used, such as for example lecithin. Lecithin may comprise a mixture of phospholipids.

In additional embodiments, an antioxidant is used. Any suitable anti-oxidant may be used such as, for example and without limitation butylated hydroxytoluene.

For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

As referenced above, the formulations of the present disclosure are generally orally administered, typically via, for example, capsules such as soft capsules. The present formulations can also be used to form transdermal patches using standard technology known in the art. Solubilized formulations of the present invention can also be formulated for intraperitoneal administration using techniques well known in the art.

In accordance with various embodiments, formulations do not include peanut oil. The lack of peanut oil obviates the risk posed to those having peanut-based allergies.

According to various embodiments described herein, a 28-day or monthly regimen of capsules can be packaged in a single kit (e.g., a blister pack) having administration days identified to improve compliance and reduce associated symptoms, among others. One or more of the capsules may contain no estradiol, for example, and/or no progesterone. Capsules that comprise no estrogen or progesterone API may be referred to as placebos. A blister pack can have a plurality of scores or perforations separating blister pack into 28 days. Each day may further comprise a single blister or a plurality of blisters. In various embodiments, each unit dose may contain micronized and/or partially solubilized, or fully solubilized progesterone and/or solubilized estradiol in amounts as set forth herein above, although other dose ranges may be contemplated. In addition, kits having other configurations are also contemplated herein. For example, without limitation, kits having such blister packs may contain any number of capsules.

Orally administered formulations of the present disclosure containing micronized and/or partially solubilized, or fully solubilized, progesterone are also used for the treatment of endometrial hyperplasia, secondary amenorrhea and other disease states treated with supplemental progesterone. Generally, progesterone-containing formulations described herein are used to treat the effects of the administration of supplemental estrogen whether administered alone or in combination with solubilized estradiol of the present disclosure or other estrogen-containing formulations. In various other embodiments, a capsule containing formulations of the present disclosure, for example a softgel capsule, may be applied in or around the vagina.

Formulations of the present disclosure containing solubilized estradiol are used to treat Estrogen-deficient States, including vasomotor symptoms, for example, in relation to treatment of hypoestrogenism related symptoms including, for example and without limitation, hot flashes and night sweats (vasomotor symptoms), sleep disturbances, mood changes, vulvo-vaginal atrophy, and osteoporosis and other non-menopausal disease states treated with supplemental estrogen.

Formulations of the present disclosure containing solubilized estradiol may be used to treat or prevent atrophic vaginitis or vulvo-vaginal atrophy. In various embodiments, a capsule, for example a softgel capsule, may be applied in or around the vagina.

Additional objects of the present disclosure includes: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

EXAMPLES

The following examples are offered to illustrate, but not to limit the claimed invention.

Example 1

Estradiol Solubility

In various experiments, suitable solvents were determined for providing sufficient solubility to make 2 mg of estradiol in a 100 mg fill mass, with a desired goal of achieving ~20 mg/g solubility for estradiol. Initial solubility experiments were done by mixing estradiol with various solvents, saturate the solution with the estradiol, equilibrate for at least 3 days and filter the un-dissolved particles and analyzing the clear supernatant for the amount of estradiol dissolved by HPLC.

Estradiol solubility experiments were performed. From this list at least one item (e.g. propylene glycol) is known to be unsuitable for encapsulation.

TABLE 1

| Ingredient | Solubility (mg/g) |
| --- | --- |
| PEG 400 | 105* |
| Propylene Glycol | 75* |
| Polysorbate 80 | 36* |
| Transcutol HP | 141 |
| Capmul PG8 | 31.2 |

*Literature reference - Salole, E. G. (1987) The Physicochemical Properties of Oestradiol, J Pharm and Biomed Analysis, 5, 635-640.

Example 2

It was desired to achieve 50 mg of progesterone suspended in a medium that can also solubilize 2 mg estradiol in a total capsule fill mass of 200 mg. In order to achieve this formulation, the required solubility of estradiol needs to be ~10 mg/g. A total fill weight of 200 mg was considered suitable for a size 5 oval soft gelatin capsule.

Additional solubility studies were performed to find solvent mixtures that might possibly be more suitable for soft gelatin encapsulation. Solubility studies were conducted with Capmul PG8 and Capmul MCM by mixing estradiol with various the solvent systems and as before by analyzing for the amount of estradiol dissolved by HPLC after filtration. Results of these experiments are presented in Table 2. It can be seen from these results that mixtures containing Miglyol:Capmul PG8 at 50%; and also Capmul MCM alone or in combination with 20% Polysorbate 80 can achieve sufficient solubility to meet the target of 10 mg/g. Capmul PG8 mixed with Miglyol at the 15 and 30% level did not provide sufficient solubility.

TABLE 2

| Ingredient | Solubility (mg/g) |
| --- | --- |
| Miglyol:Capmul PG8 (85:15) | 4.40 |
| Miglyol:Capmul PG8 (70:30) | 8.60 |
| Transcutol:Miglyol 812:Capmul PG8 (5:65:28) | >12 |
| Transcutol:Miglyol 812:Capmul PG8 (5:47:47) | >12 |
| Miglyol:Capmul PG8 (50:50) | 14.0 |
| Capmul MCM | 19.8 |
| Polysorbate 80:Capmul MCM (20:80) | 15.0 |

Example 3

Additional studies were performed to assess the stability of estradiol (4-6 mg) in solvent mixtures, as reported in Table 3. Miglyol 812 with 4% Transcutol precipitated on Hot/Cold cycling after 96 hours, while estradiol solubilized in Miglyol:Capmul blends at 30 and 50% or in Capmul MCM alone, did not precipitate under the same conditions for a minimum of 14 days.

TABLE 3

| Formulation | Estradiol mg/g | Results Hot/Cold Cycling |
|---|---|---|
| Transcutol:Miglyol 812 (4:96) | 4 | Crystallizes after 96 hours |
| Miglyol 812:Capmul PG8 (70:30) | 6 | Clear, after 14 days |
| Miglyol 812:Capmul PG8 (50:50) | 6 | Clear, after 14 days |
| Transcutol:Miglyol 812:Capmul PG8 (5:80:15) | 6 | Clear, after 14 days |
| Capmul MCM | 6 | Clear after 14 days |

12 mg estradiol solubilized in Miglyol:Capmul PG8 50:50, Capmul MCM, and in mixtures of Transcutol:Miglyol:Capmul PG8 are stable and do not precipitate for at least 12 days.

TABLE 4

| Formulation | Estradiol mg/g | Results Hot/Cold Cycling |
|---|---|---|
| Miglyol 812:Capmul PG8 (50:50) | 12 | Clear, after 12 days |
| Transcutol:Miglyol 812:Capmul PG8 (5:65:28) | 12 | Clear, after 12 days |
| Transcutol:Miglyol 812:Capmul PG8 (5:47:47) | 12 | Clear, after 12 days |
| Capmul MCM | 12 | Clear after 12 days |

Example 4

In addition to determining physical stability of the estradiol solutions over time, it is necessary to determine if the fill material will be stable during the encapsulation process. One way to test these preparations is with the addition of water to the fill mass. As can be seen in Table 5, estradiol solutions at a concentration of 6 mg/g in Polyethylene Glycol 400 and Capmul MCM are able to absorb a minimum of 7% water without recrystallization, whereas the same concentration in Miglyol 812:Capmul PG8 (75:25) precipitates.

Estradiol solutions at a concentration of 12 mg/g in Polyethylene Glycol 400 and Capmul MCM are able to absorb a minimum of 7% water without recrystallization. All Capmul PG8 containing formulations turned hazy on the addition of water. However, it should be noted that estradiol recrystallization was not observed, and the addition of water to Capmul PG 8 alone (without any estradiol) also turns hazy on the addition of water.

TABLE 5

| Formulation | Estradiol mg/g | Results after addition of 7% water |
|---|---|---|
| Miglyol 812:Capmul PG8 (75:25) | 6 | Precipitated |
| Miglyol 812:Capmul PG8 (50:50) | 12 | Hazy |
| Transcutol:Miglyol 812:Capmul PG8 (5:65:28) | 12 | Hazy |
| Capmul MCM | 12 | Clear |
| Transcutol:Miglyol 812:Capmul PG8 (5:47:47) | 12 | Hazy |
| Polyethylene Glycol 400 | 12 | clear |

Example 5

In an exemplary embodiment, a capsule is provided containing a fill material comprising:

TABLE 6

| Ingredient | Mg/Capsule |
|---|---|
| Estradiol Hemihydrate | 2.00 |
| Mono-, di- or triglyceride (Miglyol 812) | qs |
| Diethylene Glycol Monoethylether (Transcutol HP) | 65.00 |
| Liquid lecithin | 1.63 |
| Butylated Hydroxytoluene | 0.13 |
| Total Fill Weight | 325 |

Example 6

In an exemplary embodiment, a capsule is provided containing a fill material comprising:

TABLE 7

| Ingredient | Mg/Capsule |
|---|---|
| Estradiol Hemihydrate | 2.00 |
| Monoglycerides/diglycerides/triglycerides of caprylic/capric acid (Capmul MCM) | qs |
| Liquid lecithin | 1.63 |
| Polysorbate 80 | 97.5 |
| Total Fill Weight | 325 |

In an exemplary embodiment, a capsule is provided containing a fill material comprising:

TABLE 8

| Ingredient | Mg/Capsule | % w/w | Amount/Batch |
|---|---|---|---|
| Estradiol Hemihydrate | 2.03 | 0.62 | 20.2 g |
| Monoglycerides/diglycerides/triglycerides of caprylic/capric acid (Capmul MCM) | 322.97 | 99.38 | 3.23 kg |
| Total | | 100 | 3.25 kg |

The above formulation is prepared as follows: estradiol is added to Capmul MCM and mixed until dissolved.

Example 7

Progesterone Solubility

In various embodiments, both estradiol and progesterone may be dissolved in a solvent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solvent; i.e., the solubility would be 50 mg to 100 mg per capsule. Miglyol was attempted, and while it can be considered a good carrier for progesterone, it alone did not provide a desirable level of solubilization of estradiol (e.g., solubility of 12 mg/g may be desirable in various embodiments). Thus, Miglyol may be used in embodiments comprising a suspension of progesterone, though Miglyol, standing alone, is not desirable for use in embodiments having fully solubilized progesterone and/or estradiol.

As can be seen in Table 9, the solubility of progesterone in Capmul MCM is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystalization.

Based on 73 mg/g solubility, the capsule size required to make a capsule of 50 mg solubilized progesterone would be 685 mg. Therefore, it was shown that it would be feasible to make a 50 mg progesterone and 2 mg estradiol solubilized formulation. Myglyol had the lowest solubility, but that solvent is unable to dissolve the estradiol, therefore under further experiments, it was decided to proceed with the second lowest or Capmul MCM. It has also been found that 2 mg of estradiol may also be dissolved in 685 mg of Capmul MCM.

TABLE 9

| Ingredient | Progesterone Solubility (mg/g) |
| --- | --- |
| Capmul MCM | 73.4 |
| Capmul PG8 | 95 |
| Miglyol 812 | 27.8 |

In addition, it has been found that the solubility of progesterone in a solvent of Capmul MCM in combination with Gelucire 44/14 in a 9:1 ratio increases the solubility to approximately 86 mg/g. Therefore, in various embodiments, progesterone and/or estradiol may be dissolved in a Capmul MCM and Gelucire 44/14 system, wherein the ratio of Capmul MCM to Gelucire 44/14 is 9:1.

TABLE 10

| Ingredient | Progesterone Solubility (mg/g) |
| --- | --- |
| Capmul MCM:Gelucire 44/14 (9:1) | 86.4 |
| Capmul MCM:Gelucire 44/14 (7:3) | 70.5 |
| Capmul MCM:Gelucire 44/14 (6:4) | 57.4 |

Example 8

In an exemplary embodiment, a capsule is provided containing a fill material having fully solubilized progesterone and estradiol comprising:

TABLE 11

| Ingredient | Mass (mg) | % w/w | Qty/Capsule (mg) |
| --- | --- | --- | --- |
| Progesterone, USP, micronized | 50.00 | 7.14 | 50.00 |
| Estradiol Hemihydrate, USP | 2.03 | 0.29 | 2.03 |
| Capmul MCM, NF | | 82.57 | 577.97 |
| Gelucire 44/14, NF | | 10.0 | 70.00 |
| TOTAL | | 100.00 | 700.00 |

A capsule such as that shown in TABLE 11 may be manufactured in any suitable manner. For the purposes of this Example, mixing may be facilitated by an impellor, agitator, or other suitable means. Also for the purposes of this Example, heating and/or mixing may be performed under an inert or relatively inert gas atmosphere, such as nitrogen gas $N_2$. Mixing and/or heating for the purposes of this Example may be performed in any suitable vessel, such as a stainless steel vessel.

For example, Campul MCM may be heated to between 30° C. to 50° C., more preferably from 35° C. to 45° C., and more preferably to 40° C.+/−2° C. Gelucire 44/14 may be added to the Campul MCM and mixed until dissolved. The addition may occur all at once or may occur gradually over a period of time. Heat may continue to be applied during the mixing of the Gelucire 44/14 and the Campul MCM.

Heat may be removed from the Gelucire 44/14 and Campul MCM mixture. Estradiol Hemihydrate may be added to the mixture. The addition may occur all at once or may occur gradually over a period of time. Micronized progesterone may then be added to the Gelucire 44/14, Campul MCM and Estradiol Hemihydrate mixture until dissolved. The addition may occur all at once or may occur gradually over a period of time.

Example 9

In an exemplary embodiment, a capsule is provided containing a fill material having suspended progesterone comprising:

TABLE 12

| Ingredient | mg/Capsule | % | Function |
| --- | --- | --- | --- |
| Micronized Progesterone | 200.00 | 30.77 | Active |
| Medium Chain Triglyceride (MIGLYOL 812 or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 13

| Ingredient | Qty/Capsule (mg) | % w/w | Qty/Capsule (mg) | Amount/Batch (kg) |
| --- | --- | --- | --- | --- |
| Micronized Progesterone, USP | 200.00 | 33.33 | Active | 2.0 |
| Monoglycerides/diglycerides/triglycerides of caprylic/capric acid (Capmul MCM) | 394.0 | 65.67 | Carrier | 3.94 |
| Lauroyl polyoxyl-32-glycerides (Gelucire 44/14 or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE 44/14 may be added at 1% to 2% w/w to increase viscosity. The above formulation is prepared as follows: Capmul MCM is heated to about 65° C. GELUCIRE 44/14 is added and mixed until dissolved. Heat is removed. Progesterone is added and the mixture is passed through a colloid mill. The resultant fill mass can be used for encapsulation.

Example 10

In an exemplary embodiment, a capsule is provided containing a fill material having suspended progesterone comprising:

TABLE 14

| Ingredient | % | mg/Capsule | Function |
|---|---|---|---|
| Micronized Progesterone | 30.77 | 200.00 | Active |
| Medium Chain Triglyceride (MIGLYOL 812 or equivalent) | 65.93 | 428.55 | Carrier |
| Lauroyl polyoxyl-32-glycerides (Gelucire 44/14 or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL may be present in a range from about 35-95% by weight; GELUCIRE 44/14 from about 0.5-30% by weight; and BHT from about 0.01-0.1% by weight.

Example 11

For the purposes of this Example, a particle size analysis is conducted by using the Beckman Device. A sample API comprising micronized progesterone in accordance with various embodiments is provided for analysis.

Figure 4:
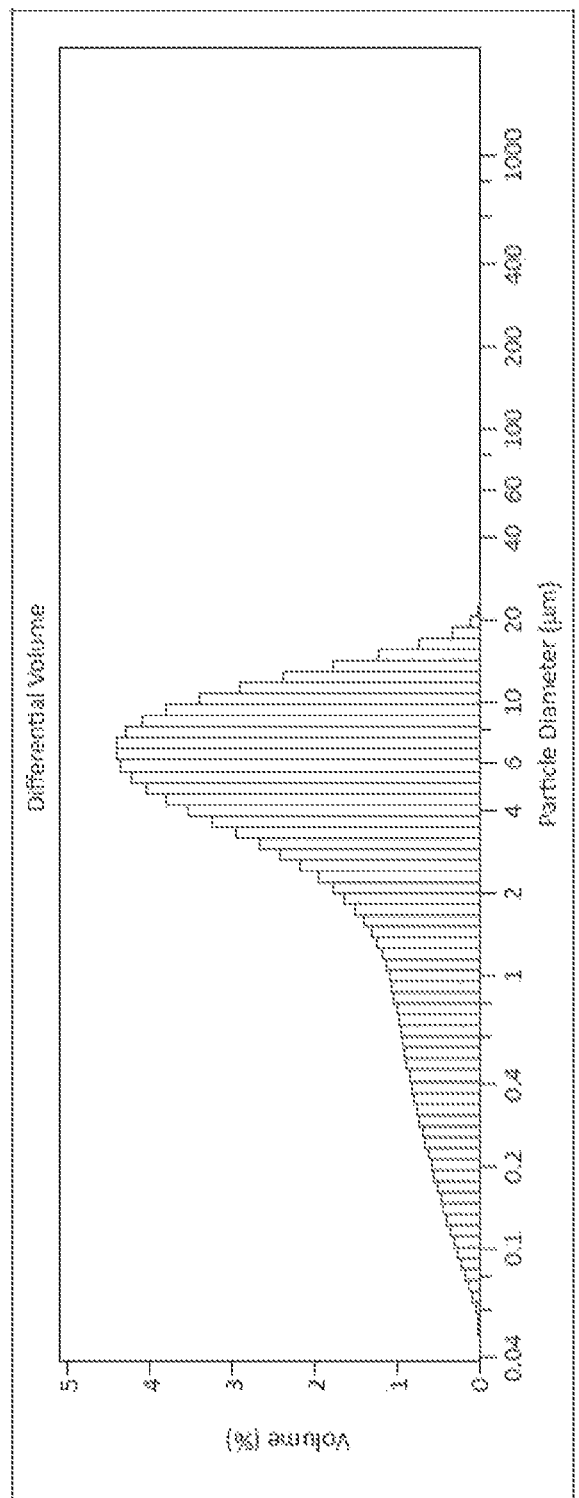
FIG. 4 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 μm, an X75 of 7.442 μm, and an X25 of 1.590 μm. The Beckman Device also yielded that the mean particle size is 4.975 μm, the median particle size is 4.279 μm, the mode particle size is 6.453 μm, and the standard deviation is 3.956 μm. A graph of the particle distribution obtained is shown in FIG. 4.

Example 12

A formulation sample having approximately 200 mg of micronized progesterone and 2 mg of estradiol was dispersed with oil. The Beckman Device, equipped with a MLM, performed analysis for 60 seconds. The Beckman Device was configured to use the Fraunhofer optical model. The Beckman Device yielded that the sample has an X50 of 11.0 μm, an X75 of 17.3 μm, and an X25 of 5.3 μm. The Beckman Device also yielded that the mean particle size is 11.8 μm, the median particle size is 11.04 μm, the mode particle size is 13.6 μm, and the standard deviation is 7.8 μm.

Example 13

In order to increase the solubility of progesterone in the final solution, Gelucire 44/14 was added at about 10% w/w.

TABLE 15

Quantitative Formula: Batch Size 10,000 capsules

| Item No. | INGREDIENT(S) | Label Claim (mg) | % w/w | Qty/Capsule (mg) | Amount/Batch (kg) |
|---|---|---|---|---|---|
| 1. | Progesterone, USP, micronized | 50.00 | 7.14 | 50.00 | 0.50 |
| 2. | Estradiol Hemihydrate, USP | 2.03 | 0.29 | 2.03 | 0.02 |
| 3. | Capmul MCM, NF | | 82.57 | 577.97 | 5.78 |
| 4. | Gelucire 44/14, NF | | 10.0 | 70.00 | 0.70 |
| | Total: | | 100.00 | 700.00 | 7.00 |

An example of the final formulation is provided in Table 15. The manufacturing process is as follows. Capmul MCM is heated to 40° C. Gelucire 44/14 is added and mixed until dissolved. Heat is removed. Estradiol is added and mixed until dissolved. Micronized progesterone is then added and mixed until dissolved.

Example 14

In an exemplary embodiment, a capsule is provided containing a fill material having fully solubilized estradiol and partially solubilized progesterone comprising:

TABLE 16

| Item No. | INGREDIENT(S) | Label Claim (mg) | % w/w | Qty/Capsule (mg) | Amount/Batch (g) |
|---|---|---|---|---|---|
| 1. | Progesterone, USP, micronized | 50.00 | 25.000 | 50.00 | 500.00 |
| 2. | Estradiol Hemihydrate | 0.25 | 0.129 | 0.26 | 2.58 |
| 3. | Capmul MCM, NF | | 73.371 | 146.74 | 1467.42 |
| 4. | Gelucire 44/14, NF | | 1.500 | 3.00 | 30.00 |
| | Total: | | 100.000 | 200.00 mg | 2000.00 |

The manufacturing process is as follows. Capmul MCM is heated to 65° C. Gelucire 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 15

In an exemplary embodiment, a capsule is provided containing a fill material having fully solubilized estradiol and partially solubilized progesterone comprising:

TABLE 17

| Item No. | INGREDIENT(S) | Label Claim (mg) | % w/w | Qty/Capsule (mg) | Amount/Batch (g) |
|---|---|---|---|---|---|
| 1. | Progesterone, USP, micronized | 200.00 | 33.33 | 200.0 | 2000.0 |
| 2. | Estradiol Hemihydrate | 2.00 | 0.35 | 2.07 | 20.7 |
| 3. | Capmul MCM, NF | | 65.32 | 391.93 | 3919.3 |
| 4. | Gelucire 44/14, NF | | 1.00 | 6.0 | 60.0 |
| | Total: | | 100.00 | 600.0 mg | 6000.0 |

The manufacturing process is as follows. Capmul MCM is heated to 65° C. Gelucire 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 16

Progesterone and Estradiol Combination Study Under Fed Conditions.

This following study protocol was used to establish bio-availability and bio-equivalence parameters for a combination product of the present disclosure comprising progesterone (200 mg) and estradiol (2.0 mg) as prepared via the process described in Example 14 and compared to 200 mg of PROMETRIUM® (Catalent Pharmaceuticals, St. Petersburg, Fla. (and 2.0 mg of ESTRACE® (Bristol-Myers Squibb Co. Princeton, N.J.), administered to twenty-four (24) normal healthy, adult human post-menopausal female subjects under fed conditions.

The Study Design: An open-label, balanced, randomized, two-treatment, two-period, two-sequence, single-dose, two-way crossover.

The subjects were housed in the clinical facility from at least 11.00 hours pre-dose to at least 48.00 hours post-dose in each period, with a washout period of at least 14 days between the successive dosing days.

Subjects were fasted for at least about 10.00 hours before being served a high-fat, high-calorie breakfast, followed by dosing, then followed by a 04.00 hour, post-dose additional period of fasting.

Standard meals were provided at about 04.00, 09.00, 13.00, 25.00, 29.00, 34.00 and 38.00 hours post-dose, respectively.

Water was restricted at least about 01 hour prior to dosing until about 01 hour post-dose (except for water given during dosing). At other times, drinking water was provided ad libitum.

Subjects were instructed to abstain from consuming caffeine and/or xanthine containing products (i.e. coffee, tea, chocolate, and caffeine-containing sodas, colas, etc.) for at least about 24.00 hours prior to dosing and throughout the study, grapefruit and\or its juice and poppy containing foods for at least about 48.00 hours prior to dosing and throughout the study.

Subjects remained seated upright for about the first 04.00 hours post-dose and only necessary movements were allowed during this period. Thereafter subjects were allowed to ambulate freely during the remaining part of the study. Subjects were not allowed to lie down (except as directed by the physician secondary to adverse events) during restriction period.

Subjects were instructed not to take any prescription medications within 14 days prior to study check in and throughout the study. Subjects were instructed not to take any over the counter medicinal products, herbal medications, etc. within 7 days prior to study check-in and throughout the study.

After overnight fasting of at least about 10.00 hours, a high-fat high-calorie breakfast was served about 30 minutes prior to administration of investigational product(s). All subjects were required to consume their entire breakfast within about 30 minutes of it being served, a single dose of either test product (T) of Progesterone 200 mg & Estradiol 2 mg tablets or the reference product (R) PROMETRIUM® (Progesterone) soft gel Capsule 200 mg and ESTRACE® (Estradiol) Tablets 2 mg (according to the randomization schedule) were administered with about 240 mL of water under fed condition, at ambient temperature in each period in sitting posture. A thorough mouth check was done to assess the compliance to dosing.

All dosed study subjects were assessed for laboratory tests at the end of the study or as applicable.

In each period, twenty-three (23) blood samples were collected. The pre-dose (10 mL) blood samples at −01.00, −00.50, 00.00 hours and the post-dose blood samples (08 mL each) were collected at 00.25, 00.50, 00.67, 00.83, 01.00, 01.33, 01.67, 02.00, 02.50, 03.00, 04.00, 05.00, 06.00, 07.00, 08.00, 10.00, 12.00, 18.00, 24.00 and 48.00 hours in labeled K2EDTA—vacutainers via an indwelling cannula placed in one of the forearm veins of the subjects. Each intravenous indwelling cannula was kept in situ as long as possible by injecting about 0.5 mL of 10 IU/mL of heparin in normal saline solution to maintain the cannula for collection of the post-dose samples. In such cases blood samples were collected after discarding the first 0.5 mL of heparin containing blood. Each cannula was removed after the 24.00 hour sample was drawn or earlier or if blocked.

At the end of the study, the samples were transferred to the bio-analytical facility in a box containing sufficient dry ice to maintain the integrity of the samples. These samples were stored at a temperature of −70° C.±20° C. in the bio-analytical facility until analysis.

Progesterone (Corrected and Uncorrected) and Estradiol (unconjugated) and estrone (total) in plasma samples is assayed using a validated LC-MS/MS method.

Fasted studies using this protocol were also conducted. However, rather than the high-fat meal prior to administration of the test and reference drug, each subject fasted for a period of at least twelve (12) hours prior to dose administration.

Example 17

Figure 2:
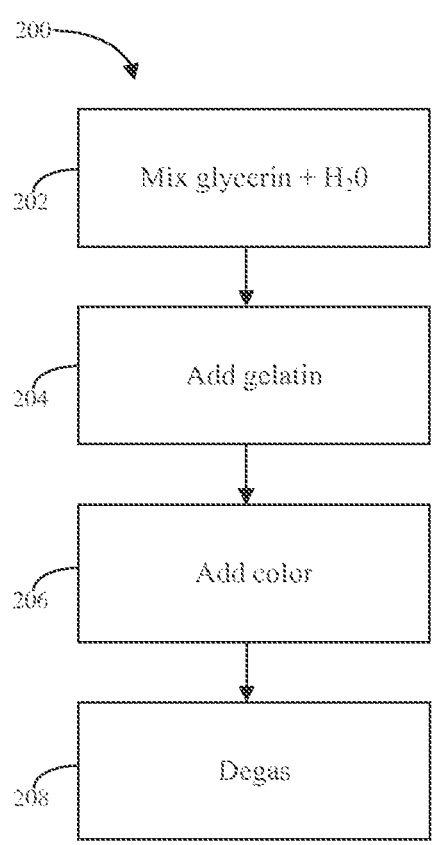
FIG. 2 illustrates an exemplary manufacturing process of a softgel material in accordance with various embodiments.
Figure 3:
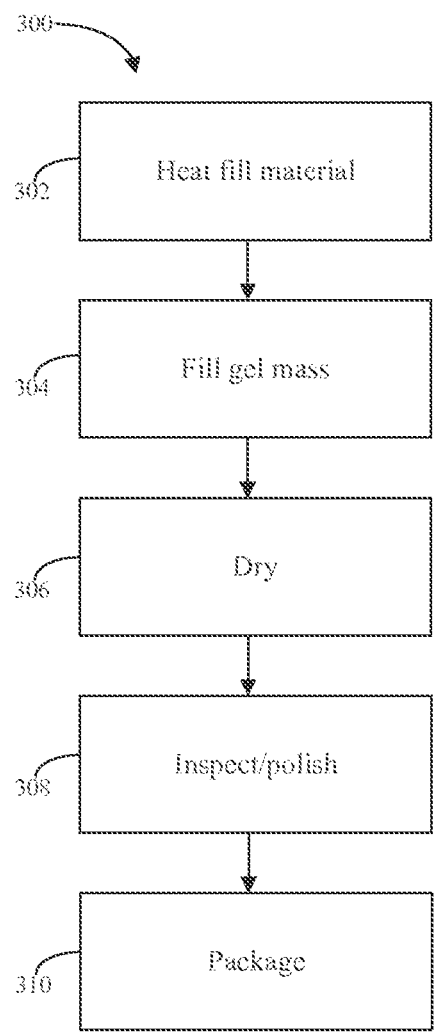
FIG. 3 illustrates an exemplary manufacturing process in accordance with various embodiments.

Method of manufacture in accordance with various embodiments are shown in FIGS. 1-3. With reference to FIG. 1, method of fill material 100 is shown. Step 102 comprises heating an oily vehicle carrier to 40° C.±5° C. Heating may be accomplished through any suitable means. The heating may be performed in any suitable vessel, such as a stainless steel vessel. The oily vehicle may be any oily vehicle described herein, for example, Capmul MCM.

Step 104 comprises mixing Gelucire 44/14 with the oily vehicle. Mixing may be facilitated by an impellor, agitator, or other suitable means. Step 102 may be performed under an inert or relatively inert gas atmosphere, such as nitrogen gas $N_2$. Mixing may be performed in any suitable vessel, such as a stainless steel vessel.

Step 106 comprises mixing estradiol into the mixture of the oily vehicle and Gelucire 44/14. Mixing may occur in a steel tank or vat. Mixing may be facilitated by an impellor, agitator, or other suitable means. Step 106 may be performed under an inert or relatively inert gas atmosphere, such as nitrogen gas $N_2$.

Step 108 comprises cooling to room temperature. Cooling may be allowed to occur without intervention or cooling may be aided by application of a cooling system.

Step 110 comprises mixing micronized progesterone into the mixture of oily vehicle, estradiol and Gelucire 44/14. Mixing may occur in a steel tank or vat. Mixing may be facilitated by an impellor, agitator, or other suitable means. Step 110 may be performed under an inert or relatively inert gas atmosphere, such as nitrogen gas $N_2$. Step 112 comprises degasing. The resulting mixture from step 112 may comprise a fill material suitable for production into a softgel capsule.

With reference to FIG. 2, softgel capsule, i.e. gel mass, production 200 is shown. Step 202 comprises mixing glycerin with water. The water used in step 202 may be purified by any suitable means, such as reverse osmosis, ozonation, filtration (e.g., through a carbon column) or the like. Mixing may be facilitated by an impellor, agitator, or other suitable means. Step 202 may be performed under an inert or relatively inert gas atmosphere, such as nitrogen gas $N_2$. Heating may be performed until the temperature reaches 80° C.±5° C.

Step 204 comprises the addition of gelatin to the glycerin water mixture. Mixing may be facilitated by an impellor, agitator, or other suitable means. Step 204 may be performed under an inert or relatively inert gas atmosphere, such as nitrogen gas $N_2$. A vacuum may be drawn in step 204 to de-aerate.

Step 206 comprises addition of a coloring agent such as a dye. A coloring agent may comprise products sold under the trademark OPATINT or other suitable agent. Step 206 may be performed under an inert or relatively inert gas atmosphere, such as nitrogen gas $N_2$. Step 208 comprises degasing. The resulting mixture from step 208 may comprise a gel capsule material suitable for use as a gel capsule in production of a softgel capsule.

With reference to FIG. 3, softgel capsule assembly process 300 is shown. Step 302 comprises heating the fill material. The fill material may be heated to any suitable temperature. In various embodiments, the fill material is heated to 30° C.+/−3° C. Fill material maybe heated in a fill hopper. A fill hopper may comprise a device configured to hold a volume of the fill material and/or to dispense the fill material in controlled volumes.

Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812 or other suitable lubricant. Step 304 thus produces one or more softgel capsules. Filling may comprise producing a ribbon of thickness 0.85 mm±0.05 mm using spreader box knobs. The fill material may be injected into the gel to produce a fill weight having target weight ±5% (i.e., 650±33 mg and 325±16.3 mg).

Step 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Step 308 may comprise inspection and/or polishing. Polishing may be performed with isopropyl alcohol. Step 310 may comprise packaging. Packaging may be accomplished through any suitable means. Packaging may comprise packing softgel capsules into a blister pack, bottle, box, pouch, or other acceptable packaging.

What is claimed is:

1. A method of treating a menopause-related symptom in a woman comprising: administering to the woman an effective amount of a pharmaceutical composition, the pharmaceutical composition comprising:
    solubilized estradiol;
    suspended progesterone; and
    a solubilizing agent;
    wherein each of the estradiol and the suspended progesterone are present in the solubilizing agent and the estradiol and progesterone are uniformly dispersed;
    wherein at least about 90% of the estradiol is solubilized in the solubilizing agent; and
    wherein the solubilizing agent comprises an effective amount at least one of mono-, di-, and triglycerides containing an ester of a C6-C12 fatty acid.

2. The method of claim 1, further comprising partially solubilized progesterone, wherein the partially solubilized progesterone is solubilized in the solubilizing agent.

3. The method of claim 1, wherein the formulation is formulated as a gelatin capsule.

4. The method of claim 1, wherein said estradiol has a dosage strength of at least about 0.125 mg and wherein said progesterone has a dosage strength of at least about 25 mg.

5. The method of claim 1, wherein the ratio of progesterone to estradiol is about 24:1, about 25:1, about 96:1, about 100:1, about 192:1, or about 200:1.

6. The method of claim 1, wherein the composition is bioequivalent to a 200 mg progesterone soft gel capsule and a 2 mg estradiol tablet.

7. A method of treating a menopause symptom in a woman comprising: administering a pharmaceutical composition to the woman, the pharmaceutical composition comprising:
    solubilized estradiol;
    suspended progesterone; and
    a solubilizing agent, the solubilizing agent comprising an effective amount mono-, di-, and triglycerides containing an ester of a C6-C12 fatty acid;
    wherein the estradiol and the suspended progesterone are present in the solubilizing agent, the estradiol and progesterone are uniformly dispersed, and at least about 90% of the estradiol is solubilized in the solubilizing agent; and
    wherein the estradiol does not precipitate for at least 14 days.

8. The method of claim 7, further comprising partially solubilized progesterone, wherein the partially solubilized progesterone is solubilized in the solubilizing agent.

9. The method of claim 7, wherein the formulation is formulated as a gelatin capsule.

10. The method of claim 7, wherein said estradiol has a dosage strength of at least about 0.125 mg and wherein said progesterone has a dosage strength of at least about 25 mg.

11. The method of claim 7, wherein the ratio of progesterone to estradiol is about 24:1, about 25:1, about 96:1, about 100:1, about 192:1, or about 200:1.

12. The method of claim 7, wherein the composition is bioequivalent to a 200 mg progesterone soft gel capsule and a 2 mg estradiol tablet.

13. A method of treating a menopause symptom comprising: administering an effective amount of a pharmaceutical composition to a woman, the pharmaceutical composition comprising:
    solubilized estradiol;
    suspended progesterone; and
    a solubilizing agent, the estradiol being stable in the solubilizing agent for at least 14 days;
    wherein each of the estradiol and the suspended progesterone are present in the solubilizing agent;
    wherein the estradiol and progesterone are uniformly dispersed;
    wherein at least about 90% of the estradiol is solubilized in the solubilizing agent, and
    wherein the solubilizing agent comprises an effective amount mono-, di-, and triglycerides containing an ester of a C6-C12 fatty acid.

14. The method of claim 13, further comprising partially solubilized progesterone, wherein the partially solubilized progesterone is solubilized in the solubilizing agent.

15. The method of claim 13, wherein the formulation is formulated as a gelatin capsule.

16. The method of claim 13, wherein said estradiol has a dosage strength of at least about 0.125 mg and wherein said progesterone has a dosage strength of at least about 25 mg.

17. The method of claim 13, wherein the ratio of progesterone to estradiol is about 24:1, about 25:1, about 96:1, about 100:1, about 192:1, or about 200:1.

18. The method of claim 13, wherein the composition is bioequivalent to a 200 mg progesterone soft gel capsule and a 2 mg estradiol tablet.

* * * * *